(12) United States Patent
Jin et al.

(10) Patent No.: US 11,040,219 B2
(45) Date of Patent: Jun. 22, 2021

(54) CLINICAL TARGET VOLUME DELINEATION METHOD AND ELECTRONIC DEVICE

(71) Applicant: Ping An Technology (Shenzhen) Co., Ltd., Shenzhen (CN)

(72) Inventors: Dakai Jin, Laurel, MD (US); Dazhou Guo, Rockville, MD (US); Le Lu, Poolesville, MD (US); Adam Patrick Harrison, Silver Spring, MD (US)

(73) Assignee: Ping An Technology (Shenzhen) Co., Ltd., Shenzhen (CN)

( * ) Notice: Subject to any disclaimer, the term of this patent is extended or adjusted under 35 U.S.C. 154(b) by 118 days.

(21) Appl. No.: 16/546,615

(22) Filed: Aug. 21, 2019

(65) Prior Publication Data

US 2021/0052918 A1  Feb. 25, 2021

(51) Int. Cl.
| | |
|---|---|
| *A61N 5/10* | (2006.01) |
| *G06T 7/00* | (2017.01) |
| *G16H 30/20* | (2018.01) |
| *G16H 30/40* | (2018.01) |
| *A61B 6/03* | (2006.01) |

(52) U.S. Cl.
CPC .......... *A61N 5/1039* (2013.01); *G06T 7/0014* (2013.01); *G16H 30/20* (2018.01); *G16H 30/40* (2018.01); *A61B 6/032* (2013.01); *A61N 2005/1074* (2013.01); *G06T 2200/24* (2013.01); *G06T 2207/10081* (2013.01); *G06T 2207/20081* (2013.01); *G06T 2207/30061* (2013.01); *G06T 2207/30096* (2013.01)

(58) Field of Classification Search
CPC ... H01L 33/465; H01L 33/06; H01L 33/0041; H01L 33/005; H01L 33/38; H01L 2933/0016; H01L 2933/0025
USPC ....................................................... 382/131
See application file for complete search history.

(56) References Cited

U.S. PATENT DOCUMENTS

2017/0084041 A1* 3/2017 Albrecht ................. G06T 7/143
2019/0192880 A1* 6/2019 Hibbard ............... A61N 5/1039

* cited by examiner

*Primary Examiner* — Amandeep Saini
(74) *Attorney, Agent, or Firm* — ScienBiziP, P.C.

(57) ABSTRACT

The present disclosure provides a clinical target volume delineation method and an electronic device. The method includes: receiving a radiotherapy computed tomography (RTCT) image; and obtaining a plurality of binary images by delineating a gross tumor volume (GTV), lymph nodes (LNs), and organs at risk (OARs) in the RTCT image. A SDMs for each of the binary images is calculated. The RTCT image and all the SDM are finally input into a clinical target volume (CTV) delineation model; and a CTV in the RTCT image is delineated by the CTV delineation model. An automatic delineation of the CTV of esophageal cancer are realized, a delineation efficiency is high and a delineation effect is good.

20 Claims, 4 Drawing Sheets

CLINICAL TARGET VOLUME DELINEATION METHOD AND ELECTRONIC DEVICE

FIELD

The present disclosure relates to a technical field of a computer in a radiotherapy planning, specifically a clinical target volume delineation method and an electronic device.

BACKGROUND

As a non-invasive treatment, radiotherapy has become a very important manners for treating malignant tumors. In order to achieve an accurate radiotherapy, a clinical target volume must be determined firstly.

At present, the determination of the clinical target volume mainly depend on manual delineation by oncologists. Delineating the clinical target area in a radiotherapy computed tomography is a huge burden even for experienced oncologists, and the delineation efficiency is low. Moreover, due to a high degree of difference between oncologists, results of the delineation may be inaccurate, which affects the outcome of the radiotherapy.

Therefore, it is necessary to provide a rapid and effective clinical target delineation manner to solve the above technical problems

SUMMARY

In order to solve the above technical problems of the prior art, embodiments of the present disclosure provide a clinical target volume delineation method and an electronic device, to overcome the technical problems that the prior art can not realize the automatic delineation of the clinical target volume, the low delineation efficiency, and the poor delineation effect.

A first aspect of an embodiment of the present disclosure provides a clinical target volume delineation method applicable in an electronic device, includes:

receiving a radiotherapy computed tomography (RTCT) image;

obtaining a plurality of binary images by delineating a gross tumor volume (GTV), lymph nodes (LNs), and organs at risk (OARs) in the RTCT image;

calculating a signed distance map (SDM) for each of the binary images;

inputting the RTCT image and all the SDM into a clinical target volume (CTV) delineation model;

delineating a CTV in the RTCT image by the CTV delineation model.

A second aspect of an embodiment of the present disclosure provides an electronic device, including:

at least one processor; and a storage device storing one or more programs which when executed by the at least one processor, causes the at least one processor to:

receive a radiotherapy computed tomography (RTCT) image;

obtain a plurality of binary images by delineating a gross tumor volume (GTV), lymph nodes (LNs), and organs at risk (OARs) in the RTCT image;

calculate a signed distance map (SDM) for each of the binary images;

input the RTCT image and all the SDM into a clinical target volume (CTV) delineation model; and delineate a CTV in the RTCT image by the CTV delineation model.

A third aspect of an embodiment of the present disclosure provides a non-transitory storage medium having stored thereon instructions that, when executed by a processor of an electronic device, causes the electronic device to perform a clinical target volume delineation method, the method includes:

receiving a radiotherapy computed tomography (RTCT) image;

obtaining a plurality of binary images by delineating a gross tumor volume (GTV), lymph nodes (LNs), and organs at risk (OARs) in the RTCT image;

calculating a signed distance map (SDM) for each of the binary images;

inputting the RTCT image and all the SDM into a clinical target volume (CTV) delineation model;

delineating a CTV in the RTCT image by the CTV delineation model.

In the embodiments of the present disclosure, by receiving a radiotherapy computed tomography (RTCT) image, obtaining a plurality of binary images by delineating a gross tumor volume (GTV), lymph nodes (LNs), and organs at risk (OARs) in the RTCT image, calculating a signed distance map (SDM) for each of the binary images, and then inputting the RTCT image and all the SDM into a clinical target volume (CTV) delineation model, a CTV in the RTCT image can be delineated by the CTV delineation model. The present disclosure can realize the automatic delineation of the CTV, and have a high delineation efficiency and a good delineation effect.

BRIEF DESCRIPTION OF THE DRAWINGS

In order to more clearly illustrate the embodiments of the present disclosure or the technical solutions in the prior art, the drawings used in the embodiments or the prior art description will be briefly introduced below. Obviously, the drawings in the following description are only some embodiments of the present disclosure, and those skilled in the art can obtain other drawings from these drawings without any creative work.

DETAILED DESCRIPTION

In order to enable those skilled in the art to better understand the solution of the present disclosure, the technical solutions in the embodiments of the present disclosure will be described below with reference to drawings in the embodiments of the present disclosure. Obviously, described embodiments are merely embodiments which are a part of the present disclosure, rather than every embodiment. All other embodiments obtained by those of ordinary skill in the art based on the embodiments of the present disclosure without creative efforts should be within the scope of the present disclosure.

Terms such as "first", "second" in the specification and claims of the present disclosure and the above drawings are used to distinguish different objects, and are not intended to describe a specific order. Moreover, terms "include" and any variations of the "include" are intended to indicate a non-exclusive inclusion. For example, a process, a method, a system, a product, or a device which includes a series of steps or units is not limited to listed steps or units, but optionally, also includes steps or units not listed, or optionally, also includes other steps or units inherent to these processes, methods, products, or equipment.

Figure 1:
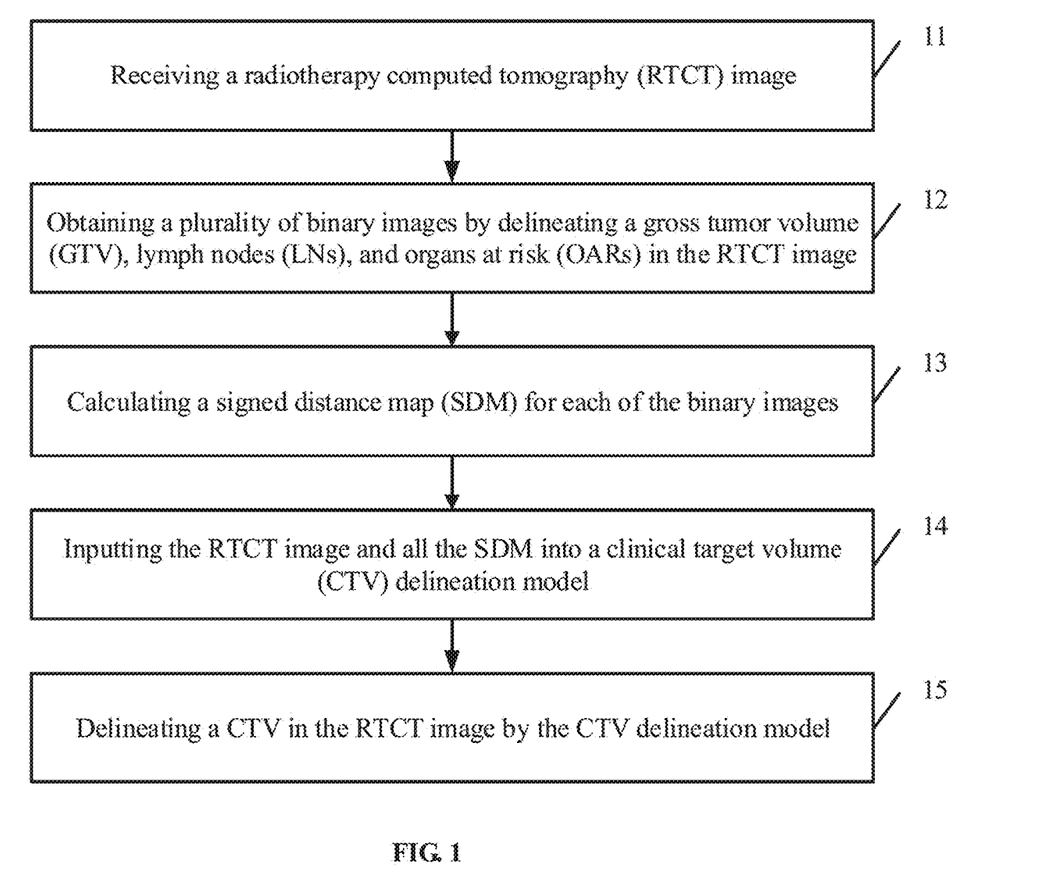
FIG. 1 shows a schematic flow chart of an embodiment of a clinical target volume delineation method according to the present disclosure.

FIG. 1 shows a schematic flow chart of an embodiment of a clinical target volume delineation method according to the present disclosure.

As shown in FIG. 1, the clinical target volume delineation method can include the following steps. According to different requirements, the order of the steps in the flow chart may be changed, and some may be omitted.

In block 11, receiving a radiotherapy computed tomography (RTCT) image.

To achieve adaptive radiotherapy for a patient with esophageal cancer, radiotherapy computed tomography (RTCT) image can be used in the radiotherapy planning to scan the affected part of the patient with esophageal cancer. By obtaining daily image information during the treatment of the patient with esophageal cancer and quantitatively monitoring the changes in the lesions, the errors caused by positions and organ movements are reduced, so that the true tolerance of a clinical target volume (CTV) can be truly evaluated, and a precise radiotherapy can be assisted.

In block 12, obtaining a plurality of binary images by delineating a gross tumor volume (GTV), lymph nodes (LNs), and organs at risk (OARs) in the RTCT image.

In order to provide spatial backgrounds/distances of anatomical structures of interest, the boundaries of the anatomical structures of interest must first be known, and the anatomical structures of interest in the RTCT image need to be delineated.

In some embodiments, the anatomical structures of interest in the RTCT image can include: a gross tumor volume (GTV), lymph nodes (LNs), and organs at risk (ORAs).

In general, when radiotherapy is performed on the patient with esophageal cancer, radioactivity easily endangers a heart, a lung, and a spinal cord. Therefore, in the present embodiment, the OARs mainly include: the heart, the lung and the spinal cord.

In an optionally embodiment of the present disclosure, the obtaining a plurality of binary images by delineating a gross tumor volume (GTV), lymph nodes (LNs), and organs at risk (OARs) in the RTCT image includes:

delineating the GTV and the LNs in the RTCT image to obtain a first binary image;

delineating the ORAs in the RTCT image by at least one pre-trained delineation model to obtain at least one second binary image.

In the optionally embodiment of the present disclosure, the GTV and the LNs in the RTCT image are delineated as a whole to obtain a binary image; the lung, the heart and the spinal cord in the RTCT image are respectively delineated to obtain three binary images.

In an optionally embodiment of the present disclosure, the delineating the GTV and the LNs in the RTCT image to obtain a first binary image includes:

displaying a user interface on a display of the electronic device, the RTCT image being displayed on the user interface;

obtain the first binary image corresponding to the GTV and the LNs by receiving the GTV and the LNs in the RTCT image manually delineated by a user.

In the optionally embodiment of the present disclosure, the RTCT image can be visually displayed on the display of the electronic device. Due to a large area of the GTV and the LNs, the GTV and the LNs in the RTCT image are automatically delineated by an experienced oncologist using a delineation tool on the visual display interface. It takes less time and more accurate delineation.

In an optionally embodiment of the present disclosure, the delineating the ORAs in the RTCT image by at least one pre-trained delineation model to obtain at least one second binary image includes;

inputting the RTCT image into a pre-trained heart delineation model, and obtaining a second binary image corresponding to the heart region by delineating the heart region in the RTCT image by the pre-trained heart delineation model;

inputting the RTCT image into a pre-trained lung delineation model, and obtaining a second binary image corresponding to the lung region by delineating the lung region in the RTCT image by the pre-trained lung delineation model;

inputting the RTCT image into a pre-trained spinal cord delineation model, and obtaining a second binary image corresponding to the spinal cord region by delineating the spinal cord region in the RTCT image by the pre-trained spinal cord delineation model.

Figure 2:
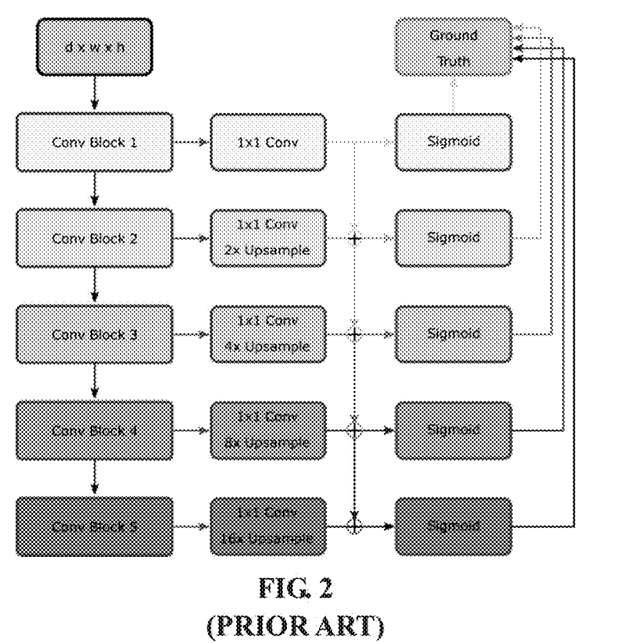
FIG. 2 shows a schematic structural diagram of a 2D progressive holistically nested network (PHNN) of the prior art.

In the optionally embodiment of the present disclosure, considering a robust performance, a low complexity, and a high computational efficiency of a 2D progressive holistically nested network (2D PHNN) in delineating pathological lungs in RTCT images, the 2D PHNN can be used to train at least one delineation model to delineate the OARs. A network structure of the 2D PHNN is shown in FIG. 2. The 2D PHNN adopts a step-by-step refinement of segmentation results, and achieves a purpose of fine segmentation by combining an intermediate prediction output and a lower layer output fusion strategy.

In an optionally embodiment of the present disclosure, the at least one delineation model can be include a heart delineation model, a lung delineation model, and a spinal cords delineation model.

The heart delineation is taken as an example to illustrate a training process of the heart delineation model. A training process of the lung delineation model, and a training process of the spinal cords delineation model, such as the training process of the heart delineation model, is not elaborated.

Specifically, the training process of the heart delineation model may include:

Collect a plurality of RTCT images;

Labeling a heart region in each of the RTCT images:

Dividing the labeled RTCT images into a training data set and a verification data set;

Inputting the training data set into the 2D PHNN to obtained the hurt delineation model:

Inputting the verification data set into the hurt delineation model for verification;

Determining whether a verification pass rate is greater than a preset pass rate threshold;

Ending a training process of the hurt delineation model, when the verification pass rate is greater than or equal to the preset pass rate threshold;

Re-dividing the labeled RTCT image into a training data set and a verification data set, when the verification pass rate is less than the preset pass rate threshold, and re-training a new hurt delineation model based on the new training data set until the verification pass rate is greater than or equal to the preset pass rate threshold.

In the optionally embodiment of the present disclosure, multiple RTCT images of the patients with esophageal cancer can be collected from a hospital imaging department, and the corresponding annotation data can be obtained from an annotation platform. The annotation data can include delineation data of the hearts, the lungs, and the spinal cords of the patients with esophageal cancer. Data acquisition is easier and application range is wider because it is only need to acquire the RTCT images and the corresponding annotation data.

The hearts area, the lungs area, and the spinal cords area in the RTCT images are distinguished by different labels. For example, a label "0" represents background, a label "1" represents esophageal area, a label "2" a label "2" represents the hearts area, a label "3" represents the spinal cords area, a label "4" represents left lungs area, and a label "5" represents right lungs area.

The labeled RTCT images are used as the original data set, 80% of the original data is used as the training data set for training the hurt (or the lung, the spinal cord) delineation model, and 20% of the original data is used as the verification data set for vivificating the hurt (or the lung, the spinal cord) delineation model.

In block 13, calculating a signed distance map (SDM) for each of the binary images.

In order to encode a spatial background of the GTV and the LNs, the SDM of the GTV and the LNs should be calculated. Simultaneously, in order to encode a spatial background of the OARs, the SDM of the OARs should be calculated.

The signature distance map can be calculated using a distance map algorithm. The distance map algorithm is a special transform for raster images, which transforms a binary image into a grayscale image, where a gray value of each pixel is equal to its closest distance to the adjacent object on a raster map. That is, the SDM is produced from a binary image, where the value in each voxel measures the distance to the closest object boundary. Voxels inside and outside the boundary have positive and negative values, respectively. More formally, let $O_i$ denote a binary mask, where i $\in$ {GTV+LNs, lung, heart, spinal cord} and let $\Gamma(\cdot)$ be a function that computes boundary voxels of a binary image. The SDMs value at a voxel p with respect to O is computed as:

$$SDM_{\Gamma(O_i)}(p) = \begin{cases} \min_{q \in \Gamma(O_i)} d(p, q) & \text{if } p \notin O_i \\ -\min_{q \in \Gamma(O_i)} d(p, q) & \text{if } p \in O_i \end{cases} \quad (1)$$

where d(p, q) is a Euclidean distance measure from p to q. A process of calculating a SDM is prior art, and the present disclosure will not be will not be described in detail herein.

In the embodiments, by calculating the SDMs of the GTV+LNs, the lung, the heart, and the spinal cord, and then inputting the SDMs into the CTV delineation model, the CTV delineation model can more easily consider influences of the GTV, the LNs and the OARs on a boundary of CTV, and better simulate an inference process of oncologists on CTV.

In block 14, inputting the RTCT image and all the SDM into a clinical target volume (CTV) delineation model.

In order to improve a computational efficiency, the CTV delineation model can be trained in advance using a 3D PHNN.

In an optionally embodiment of the present disclosure, a training process of the CTV delineation model can include:
collecting a plurality of RTCT images;
obtaining a plurality of binary images corresponding to each of the collected RTCT images by delineating a GTV, LNs, and OARs in each of the collected RTCT images;
calculating a SDM for each of the obtained binary images;
enhancing each the calculated SDM;
inputting the RTCT images and all the enhanced SDM to a 3D progressive holistically nested network (PHNN) for training to obtain the CTV delineation model.

In the optionally embodiment of the present disclosure, in order to improve a robustness of the CTV delineation model, after calculating a SDM for each of the obtained binary images, the SDMs need to be enhanced. The CTV delineation model can be trained based on the enhanced SDMs.

In an optionally embodiment of the present disclosure, the SDMs can be enhanced in the following four manners:

A first manner: shaking the binary image corresponding to the GTV+LNs, and manually delineating the OARs in the RTCT images.

A second manner: shaking the binary image corresponding to the GTV+LNs, and delineating the OARs in the RTCT images by the ORAs delineation model.

A third manner: do not jitter the binary image corresponding to the GTV+LNs, and manually delineating the OARs in the RTCT images.

A fourth manner: do not jitter the binary image corresponding to the GTV+LNs, and delineating the OARs in the RTCT images by the ORAs delineation model.

Through the above four manners to enhance each the calculated SDM, a small number of data sets can be expanded into a large number of data sets. Increasing the data set of training the CTV delineation model is beneficial to improve a generalization ability of CTV delineation model, so that the CTV delineation model can delineate a better CTV for any kind of RTCT images.

In an optionally embodiment of the present disclosure, the enhancing each the calculated SDM includes:
jittering each pixel point in each the calculated SDM within a preset range, wherein the jittering comprises: spatial translations.

In the optionally embodiment of the present disclosure, the preset range can be 4*4*4 cubic millimeters.

According to an experience, when a tumor oncologist manually delineates a CTV in a RTCT image, there will be an error of 4*4*4 cubic millimeters. Therefore, by limiting shaking the range of the voxel to 4*4*4 cubic millimeters, it is possible to simulate the delineation of CTV by the tumor oncologists, thus effectively improving the performance of the CTV delineation models.

In addition, in order to increase the data set for training the CTV delineation model, 96*96*64 VOI patches can be extracted in the following two manners: (1) in order to obtain enough VOI patches with positive CTV content, VOI of the CTV center can be randomly extracted; (2) in order to obtain enough VOI patches with negative CTV content, 20 VOI patches can be randomly extracted from the entire CTV.

In an optionally embodiment of the present disclosure, after calculating the SDMs for each of the binary images, the method further includes:
fixing the RTCT images and all the SDM to a preset size;
extracting a preset number of volume of interest (VOI) patches from the RTCT images and all the SDM.

In the optionally embodiment of the present disclosure, since the RTCT images has a voxel size of 412*412*250, if the RTCT images are directly input into the CTV delineation model, it will result in a large amount of data calculation, and the CTV delineation model delineates the CTVs in the RTCT images takes a long time. Therefore, in order to further improve the efficiency of the CTV delineation model to delineate the CTV, the RTCT images and SDMs images can be resampled to a fixed resolution, for example, 1.0× 1.0×2.5 mm.

In block 15, delineating a CTV in the RTCT image by the CTV delineation model.

In some embodiments, after the CTV delineation model delineates the CTV in the RTCT image, a user interface can be displayed on the display of the electronic device, and the delineated CTV can be displayed on the user interface.

The clinical target area delineation method provided by the embodiment of the present disclosure, by receiving a radiotherapy computed tomography (RTCT) image, obtaining a plurality of binary images by delineating a gross tumor volume (GTV), lymph nodes (LNs), and organs at risk (OARs) in the RTCT image, calculating a signed distance map (SDM) for each of the binary images, and then inputting the RTCT image and all the SDM into a clinical target volume (CTV) delineation model, a CTV in the RTCT image can be delineated by the CTV delineation model. The present disclosure can realize the automatic delineation of the CTV of esophageal cancer, and have a high efficiency and a good delineation effect.

Figure 3:
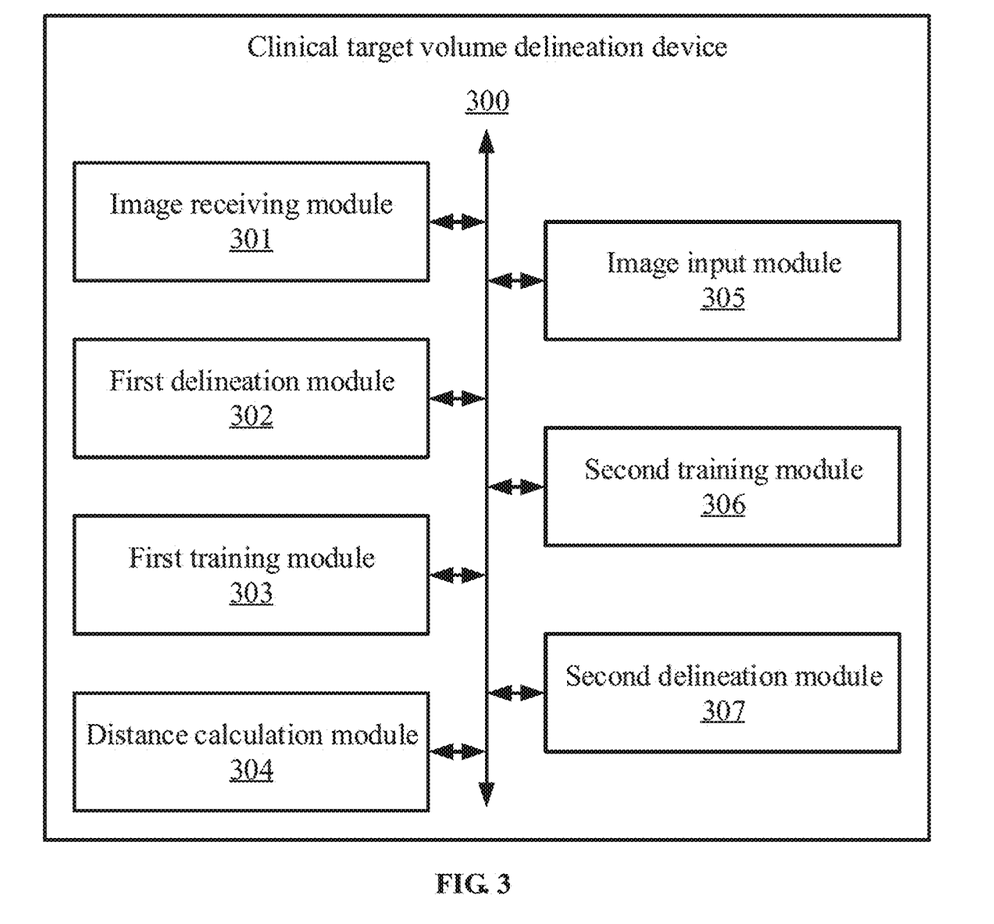
FIG. 3 shows a schematic structural diagram of a clinical target volume delineation device according to the present disclosure.

FIG. 3 shows a schematic structural diagram of a clinical target volume delineation device according to the present disclosure.

In some embodiments, the clinical target volume delineation device 300 can include a plurality of function modules consisting of program code segments. The program code of each program code segments in the clinical target volume delineation device 300 may be stored in a storage device of an electronic device and executed by the at least one processor to perform (described in detail in FIG. 1) a function of automatically delineating a clinical target volume.

In an embodiment, the clinical target volume delineation device 300 can be divided into a plurality of functional modules, according to the performed functions. The functional module can include: an image receiving module 301, a first delineation module 302, a first training module 303, a distance calculation module 304, an image input module 305, a second training module 306, and a second delineation module 307. A module as referred to in the present disclosure refers to a series of computer program segments that can be executed by at least one processor and that are capable of performing fixed functions, which are stored in a storage device. In this embodiment, the functions of each module will be detailed in the following embodiments.

The image receiving module 301, is configured to receive a radiotherapy computed tomography (RTCT) image.

To achieve adaptive radiotherapy for a patient with esophageal cancer, radiotherapy computed tomography (RTCT) image can be used in the radiotherapy planning to scan the affected part of the patient with esophageal cancer. By obtaining daily image information during the treatment of the patient with esophageal cancer and quantitatively monitoring the changes in the lesions, the errors caused by positions and organ movements are reduced, so that the true tolerance of a clinical target volume (CTV) can be truly evaluated, and a precise radiotherapy can be assisted.

The first delineation module 302, is configured to delineate a gross tumor volume (GTV) area, lymph nodes (LNs), and organs at risk (OARs) in the RTCT image to obtain a plurality of binary images.

In order to provide spatial backgrounds/distances of anatomical structures of interest, the boundaries of the anatomical structures of interest must first be known, and the anatomical structures of interest in the RTCT image need to be delineated.

In some embodiments, the anatomical structures of interest in the RTCT image can include: a gross tumor volume (GTV), lymph nodes (LNs), and organs at risk (ORAs).

In general, when radiotherapy is performed on the patient with esophageal cancer, radioactivity easily endangers a heart, a lung, and a spinal cord. Therefore, in the present embodiment, the OARs mainly include: the heart, the lung and the spinal cord.

In an optionally embodiment of the present disclosure, the first delineation module 302 is specifically configured to:
delineate the GTV and the LNs in the RTCT image to obtain a first binary image;
delineate the ORAs in the RTCT image by at least one pre-trained delineation model to obtain at least one second binary image.

In the optionally embodiment of the present disclosure, the GTV and the LNs in the RTCT image are delineated as a whole to obtain a binary image; the lung, the heart and the spinal cord in the RTCT image are respectively delineated to obtain three binary images.

In an optionally embodiment of the present disclosure, the delineate the GTV and the LNs in the RTCT image to obtain a first binary image includes:
display a user interface on a display of the electronic device, the RTCT image being displayed on the user interface;
obtain the first binary image corresponding to the GTV and the LNs by receiving the GTV and the LNs in the RTCT image manually delineated by a user.

In the optionally embodiment of the present disclosure, the RTCT image can be visually displayed on the display of the electronic device. Due to a large area of the GTV and the LNs, the GTV and the LNs in the RTCT image are automatically delineated by an experienced oncologist using a delineation tool on the visual display interface. It takes less time and more accurate delineation.

In an optionally embodiment of the present disclosure, the delineate the ORAs in the RTCT image by at least one pre-trained delineation model to obtain at least one second binary image includes:
input the RTCT image into a pre-trained heart delineation model, and obtaining a second binary image corresponding to the heart region by delineating the heart region in the RTCT image by the pre-trained heart delineation model;
input the RTCT image into a pre-trained lung delineation model, and obtaining a second binary image corresponding to the lung region by delineating the lung region in the RTCT image by the pre-trained lung delineation model;
inputting the RTCT image into a pre-trained spinal cord delineation model, and obtaining a second binary image corresponding to the spinal cord region by delineating the spinal cord region in the RTCT image by the pre-trained spinal cord delineation model.

In the optionally embodiment of the present disclosure, considering a robust performance, a low complexity, and a high computational efficiency of a 2D progressive holistically nested network (2D PHNN) in delineating pathological lungs in RTCT images, the 2D PHNN can be used to train at least one delineation model to delineate the OARs. A network structure of the 2D PHNN is shown in FIG. 2. The 2D PHNN adopts a step-by-step refinement of segmentation results, and achieves a purpose of fine segmentation by combining an intermediate prediction output and a lower layer output fusion strategy.

In an optionally embodiment of the present disclosure, the at least one delineation model can be include a heart delineation model, a lung delineation model, and a spinal cords delineation model.

The first training module 303, is configured to train the at least one delineation model.

The heart delineation is taken as an example to illustrate a training process of the heart delineation model. A training process of the lung delineation model, and a training process of the spinal cords delineation model, such as the training process of the heart delineation model, is not elaborated.

Specifically, the training process of the heart delineation model may include:

Collect a plurality of RTCT images;

Labeling a heart region in each of the RTCT images;

Dividing the labeled RTCT images into a training data set and a verification data set;

Inputting the training data set into the 2D PHNN to obtained the hurt delineation model;

Inputting the verification data set into the hurt delineation model for verification;

Determining whether a verification pass rate is greater than a preset pass rate threshold;

Ending a training process of the hurt delineation model, when the verification pass rate is greater than or equal to the preset pass rate threshold;

Re-dividing the labeled RTCT image into a training data set and a verification data set, when the verification pass rate is less than the preset pass rate threshold, and re-training a new hurt delineation model based on the new training data set until the verification pass rate is greater than or equal to the preset pass rate threshold.

In the optionally embodiment of the present disclosure, multiple RTCT images of the patients with esophageal cancer can be collected from a hospital imaging department, and the corresponding annotation data can be obtained from an annotation platform. The annotation data can include delineation data of hurt the hearts, the lungs, and the spinal cords of the patients with esophageal cancer. Data acquisition is easier and application range is wider because it is only need to acquire the RTCT images and the corresponding annotation data.

The hearts area, the lungs area, and the spinal cords area in the RTCT images are distinguished by different labels. For example, a label "0" represents background, a label "1" represents esophageal area, a label "2" a label "2" represents the hearts area, a label "3" represents the spinal cords area, a label "4" represents left lungs area, and a label "5" represents right lungs area.

The labeled RTCT images are used as the original data set, 80% of the original data is used as the training data set for training the hurt (or the lung, the spinal cord) delineation model, and 20% of the original data is used as the verification data set for vivificating the hurt (or the lung, the spinal cord) delineation model.

The distance calculation module 304, is configured to calculate a signed distance map (SDM) for each of the binary images.

In order to encode a spatial background of the GTV and the LNs, the SDM of the GTV and the LNs should be calculated. Simultaneously, in order to encode a spatial background of the OARs, the SDM of the OARs should be calculated.

The signature distance map can be calculated using a distance map algorithm. The distance map algorithm is a special transform for raster images, which transforms a binary image into a grayscale image, where a gray value of each pixel is equal to its closest distance to the adjacent object on a raster map. That is, the SDM is produced from a binary image, where the value in each voxel measures the distance to the closest object boundary. Voxels inside and outside the boundary have positive and negative values, respectively. More formally, let $O_i$ denote a binary mask, where i $\in$ {GTV+LNs, lung, heart, spinal cord} and let $\Gamma(\cdot)$ be a function that computes boundary voxels of a binary image. The SDMs value at a voxel p with respect to O is computed as:

$$SDM_{\Gamma(O_i)}(p) = \begin{cases} \min_{q \in \Gamma(O_i)} d(p, q) & \text{if } p \notin O_i \\ -\min_{q \in \Gamma(O_i)} d(p, q) & \text{if } p \in O_i \end{cases} \quad (1)$$

where d(p, q) is a Euclidean distance measure from p to q. A process of calculating a SDM is prior art, and the present disclosure will not be will not be described in detail herein.

In the embodiments, by calculating the SDMs of the GTV+LNs, the lung, the heart, and the spinal cord, and then inputting the SDMs into the CTV delineation model, the CTV delineation model can more easily consider influences of the GTV, the LNs and the OARs on a boundary of CTV, and better simulate an inference process of oncologists on CTV.

The image input module 305, is configured to input the RTCT image and all the SDM into a clinical target volume (CTV) delineation model.

In order to improve a computational efficiency, the CTV delineation model can be trained in advance using a 3D PHNN.

The second training module 306, is configured to train the CTV delineation model.

In an optionally embodiment of the present disclosure, a training process of the CTV delineation model can include:

collecting a plurality of RTCT images;

obtaining a plurality of binary images corresponding to each of the collected RTCT images by delineating a GTV, LNs, and OARs in each of the collected RTCT images;

calculating a SDM for each of the obtained binary images;

enhancing each the calculated SDM;

inputting the RTCT images and all the enhanced SDM to a 3D progressive holistically nested network (PHNN) for training to obtain the CTV delineation model.

In the optionally embodiment of the present disclosure, in order to improve a robustness of the CTV delineation model, after calculating a SDM for each of the obtained binary images, the SDMs need to be enhanced. The CTV delineation model can be trained based on the enhanced SDMs.

In an optionally embodiment of the present disclosure, the SDMs can be enhanced in the following four manners:

A first manner: shaking the binary image corresponding to the GTV+LNs, and manually delineating the OARs in the RTCT images.

A second manner: shaking the binary image corresponding to the GTV+LNs, and delineating the OARs in the RTCT images by the ORAs delineation model.

A third manner: do not jitter the binary image corresponding to the GTV+LNs, and manually delineating the OARs in the RTCT images.

A fourth manner: do not jitter the binary image corresponding to the GTV+LNs, and delineating the OARs in the RTCT images by the ORAs delineation model.

Through the above four manners to enhance each the calculated SDM, a small number of data sets can be expanded into a large number of data sets. Increasing the data set of training the CTV delineation model is beneficial to improve a generalization ability of CTV delineation model, so that the CTV delineation model can delineate a better CTV for any kind of RTCT images.

In an optionally embodiment of the present disclosure, the enhancing each the calculated SDM includes:

jittering each pixel point in each the calculated SDM within a preset range, wherein the jittering comprises: spatial translations.

In the optionally embodiment of the present disclosure, the preset range can be 4*4*4 cubic millimeters.

According to an experience, when a tumor oncologist manually delineates a CTV in a RTCT image, there will be an error of 4*4*4 cubic millimeters. Therefore, by limiting shaking the range of the voxel to 4*4*4 cubic millimeters, it is possible to simulate the delineation of CTV by the tumor oncologists, thus effectively improving the performance of the CTV delineation models.

In addition, in order to increase the data set for training the CTV delineation model, 96*96*64 VOI patches can be extracted in the following two manners: (1) in order to obtain enough VOI patches with positive CTV content, VOI of the CTV center can be randomly extracted; (2) in order to obtain enough VOI patches with negative CTV content, 20 VOI patches can be randomly extracted from the entire CTV.

In an optionally embodiment of the present disclosure, after calculating the SDMs for each of the binary images, the device further includes:

a fixing module, is configured to fix the RTCT images and all the SDM to a preset size;

an extraction module, is configured to extract a preset number of volume of interest (VOI) patches from the RTCT images and all the SDM.

In the optionally embodiment of the present disclosure, since the RTCT images has a voxel size of 412*412*250, if the RTCT images are directly input into the CTV delineation model, it will result in a large amount of data calculation, and the CTV delineation model delineates the CTVs in the RTCT images takes a long time. Therefore, in order to further improve the efficiency of the CTV delineation model to delineate the CTV, the RTCT images and SDMs images can be resampled to a fixed resolution, for example, 1.0× 1.0×2.5 mm.

The second delineation module 307, is configured to delineate a CTV in the RTCT image by the CTV delineation model.

In some embodiments, after the CTV delineation model delineates the CTV in the RTCT image, a user interface can be displayed on the display of the electronic device, and the delineated CTV can be displayed on the user interface.

The clinical target area delineation device provided by the embodiment of the present disclosure, by receiving a radiotherapy computed tomography (RTCT) image, obtaining a plurality of binary images by delineating a gross tumor volume (GTV), lymph nodes (LNs), and organs at risk (OARs) in the RTCT image, calculating a signed distance map (SDM) for each of the binary images, and then inputting the RTCT image and all the SDM into a clinical target volume (CTV) delineation model, a CTV in the RTCT image can be delineated by the CTV delineation model. The present disclosure can realize the automatic delineation of the CTV of esophageal cancer, and have a high efficiency and a good delineation effect.

Figure 4:
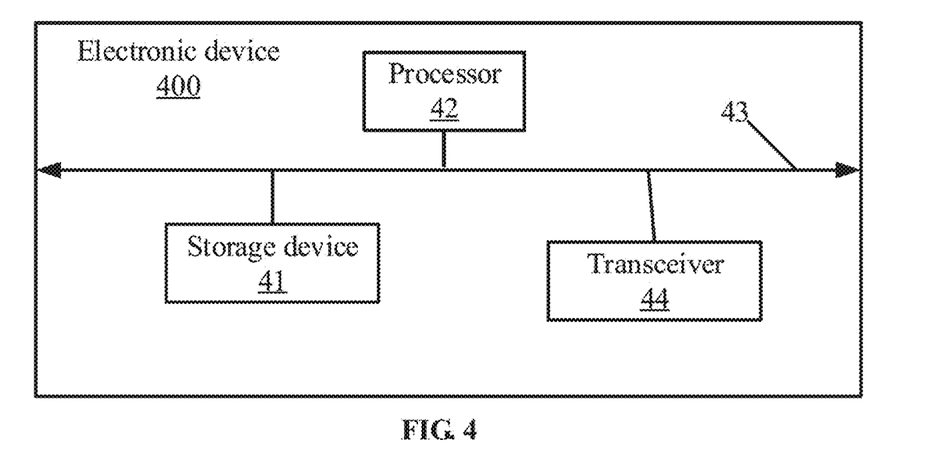
FIG. 4 shows a schematic structural diagram of an electronic device according to the present disclosure.

FIG. 4 shows a schematic structural diagram of an electronic device according to an embodiment of the present disclosure.

As shown in FIG. 4, the electronic device 400 may include: at least one storage device 41, at least one processor 42, at least one communication bus 43, and a transceiver 44.

It should be understood by those skilled in the art that the structure of the electronic device 400 shown in FIG. 4 does not constitute a limitation of the embodiment of the present disclosure. The electronic device 400 may be a bus type structure or a star type structure, and the electronic device 400 may also include more or less hardware or software than illustrated, or may have different component arrangements.

In at least one embodiment, the electronic device 400 can include a terminal that is capable of automatically performing numerical calculations and/or information processing in accordance with pre-set or stored instructions. The hardware of the terminal can include, but is not limited to, a microprocessor, an application specific integrated circuit, programmable gate arrays, digital processors, and embedded devices. The electronic device 400 may further include a client device. The client device may include, but is not limited to, any electronic product that can interact with the client through a keyboard, a mouse, a remote controller, a touch panel or a voice control device, for example, an individual computers, tablets, smartphones, digital cameras, etc.

It should be noted that the electronic device 400 is merely an example, and other existing or future electronic products may be included in the scope of the present disclosure, and are included in the reference.

In some embodiments, the storage device 41 can be used to store program codes of computer readable programs and various data, such as the clinical target volume delineation device 300 installed in the electronic device 400, and automatically access to the programs or data with high speed during running of the electronic device 400. The storage device 41 can include a read-only memory (ROM), a programmable read-only memory (PROM), an erasable programmable read only memory (EPROM), an one-time programmable read-only memory (OTPROM), an electronically-erasable programmable read-only memory (EEPROM) ), a compact disc read-only memory (CD-ROM), or other optical disk storage, magnetic disk storage, magnetic tape storage, or any other storage medium readable by the electronic device 400 that can be used to carry or store data.

In some embodiments, the at least one processor 42 may be composed of an integrated circuit, for example, may be composed of a single packaged integrated circuit, or may be composed of multiple integrated circuits of same function or different functions. The at least one processor 42 can include one or more central processing units (CPU), a microprocessor, a digital processing chip, a graphics processor, and various control chips. The at least one processor 42 is a control unit of the electronic device 400, which connects various components of the electronic device 400 using various interfaces and lines. By running or executing a computer program or modules stored in the storage device 41, and by invoking the data stored in the storage device 41, the at least one processor 42 can perform various functions of the electronic device 400 and process data of the electronic device 400.

In some embodiments, the least one bus 43 is used to achieve communication between the storage device 41 and the at least one processor 42, and other components of the electronic device 400.

Although it is not shown, the electronic device 400 may further include a power supply (such as a battery) for powering various components. Preferably, the power supply may be logically connected to the at least one processor 42 through a power management device, thereby, the power management device manages functions such as charging, discharging, and power management. The power supply may include one or more a DC or AC power source, a recharging device, a power failure detection circuit, a power converter or inverter, a power status indicator, and the like. The electronic device 400 may further include various sensors, such as a BLUETOOTH module, a Wi-Fi module, and the like, and details are not described herein.

It should be understood that the described embodiments are for illustrative purposes only and are not limited by the scope of the present disclosure.

The above-described integrated unit implemented in a form of software function modules can be stored in a computer readable storage medium. The above software function modules are stored in a storage medium, and includes a plurality of instructions for causing a computer device (which may be a personal computer, an electronic device, or a network device, etc.) or a processor to execute the method according to various embodiments of the present disclosure.

In a further embodiment, in conjunction with FIG. 1, the at least one processor 42 can execute an operating device and various types of applications (such as the clinical target volume delineation device 300) installed in the electronic device 400, program codes, and the like. For example, the at least one processor 42 can execute the modules 301-307.

In at least one embodiment, the storage device 41 stores program codes. The at least one processor 42 can invoke the program codes stored in the storage device 41 to perform related functions. For example, the modules described in FIG. 3 are program codes stored in the storage device 41 and executed by the at least one processor 42, to implement the functions of the various modules.

In at least one embodiment, the storage device 41 stores a plurality of instructions that are executed by the at least one processor 42 to implement all or part of the steps of the method described in the embodiments of the present disclosure.

Specifically, the storage device 41 stores the plurality of instructions which when executed by the at least one processor 42, causes the at least one processor 42 to:

receive a radiotherapy computed tomography (RTCT) image;

obtain a plurality of binary images by delineating a gross tumor volume (GTV), lymph nodes (LNs), and organs at risk (OARs) in the RTCT image:

calculate a signed distance map (SDM) for each of the binary images:

input the RTCT image and all the SDM into a clinical target volume (CTV) delineation model; and delineate a CTV in the RTCT image by the CTV delineation model.

In at least one embodiment, the at least one processor to obtain a plurality of binary images by delineating a gross tumor volume (GTV), lymph nodes (LNs), and organs at risk (OARs) in the RTCT image includes:

delineate the GTV and the LNs in the RTCT image to obtain a first binary image;

delineate the ORAs in the RTCT image by at least one pre-trained delineation model to obtain at least one second binary image.

In at least one embodiment, the at least one processor to delineate the GTV and the LNs in the RTCT image to obtain a first binary image comprises:

display a user interface on a display of the electronic device, the RTCT image being displayed on the user interface;

obtain the first binary image corresponding to the GTV and the LNs by receiving the GTV and the LNs in the RTCT image manually delineated by a user.

In at least one embodiment, the ORAs comprises: a heart region, a lung region, and a spinal cord.

In at least one embodiment, the at least one processor to delineate the ORAs in the RTCT image by at least one pre-trained delineation model to obtain at least one second binary image includes:

input the RTCT image into a pre-trained heart delineation model, and obtain a second binary image corresponding to the heart region by delineating the heart region in the RTCT image by the pre-trained heart delineation model;

input the RTCT image into a pre-trained lung delineation model, and obtain a second binary image corresponding to the lung region by delineating the lung region in the RTCT image by the pre-trained lung delineation model;

input the RTCT image into a pre-trained spinal cord delineation model, and obtain a second binary image corresponding to the spinal cord region by delineating the spinal cord region in the RTCT image by the pre-trained spinal cord delineation model.

In at least one embodiment, the at least one processor further to:

collect a plurality of RTCT images;

obtain a plurality of binary images corresponding to each of the collected RTCT images by delineating a GTV, LNs, and OARs in each of the collected RTCT images;

calculate a SDM for each of the obtained binary images;

enhance each the calculated SDM;

input the RTCT images and the corresponding enhanced SDM to a 3D progressive holistically nested network (PHNN) for training to obtain the CTV delineation model.

In at least one embodiment, the at least one processor to enhance each the calculated SDM includes:

jitter each pixel point in each the calculated SDM within a preset range, wherein the jitter includes: spatial translations.

In at least one embodiment, wherein the at least one processor further to:

fix the RTCT images and all the SDM to a preset size, after calculating the SDMs for each of the binary images;

extract a preset number of volume of interest (VOI) patches from the RTCT images and all the SDM.

The embodiment of the present disclosure further provides a computer storage medium, and the computer storage medium store a program that performs all or part of the steps including any of the method described in the above embodiments.

It should be noted that, for a simple description, the above method embodiments expressed as a series of action combinations, but those skilled in the art should understand that the present disclosure is not limited by the described action sequence. According to the present disclosure, some steps in the above embodiments can be performed in other sequences or simultaneously. Secondly, those skilled in the art should also understand that the embodiments described in the specification are all optional embodiments, and the actions and units involved are not necessarily required by the present disclosure.

In the above embodiments, descriptions of each embodiment has different focuses, and when there is no detail part in a certain embodiment, please refer to relevant parts of other embodiments.

In several embodiments provided in the preset application, it should be understood that the disclosed apparatus can be implemented in other ways. For example, the device embodiments described above are merely illustrative. For example, divisions of the unit are only a logical function division, and there can be other division ways in actual implementation.

The modules described as separate components may or may not be physically separated, and the components displayed as modules may or may not be physical units. That is, it can locate in one place, or distribute to multiple network units. Some or all of the modules can be selected according to actual needs to achieve the purpose of the solution of above embodiments.

In addition, each functional unit in each embodiment of the present disclosure can be integrated into one processing unit, or can be physically present separately in each unit, or two or more units can be integrated into one unit. The above integrated unit can be implemented in a form of hardware or in a form of a software functional unit.

It is apparent to those skilled in the art that the present disclosure is not limited to the details of the above-described exemplary embodiments, and the present disclosure can be embodied in other specific forms without departing from the spirit or essential characteristics of the present disclosure. Therefore, the present embodiments are to be considered as illustrative and not restrictive, and the scope of the present disclosure is defined by the appended claims instead all changes in the meaning and scope of equivalent elements are included in the present disclosure. Any reference signs in the claims should not be construed as limiting the claim.

The above embodiments are only used to illustrate technical solutions of the present disclosure, rather than restrictions on the technical solutions. Although the present disclosure has been described in detail with reference to the above embodiments, those skilled in the art should understand that the technical solutions described in one embodiments can be modified, or some of technical features can be equivalently substituted, and these modifications or substitutions do not detract from the essence of the corresponding technical solutions from the scope of the technical solutions of the embodiments of the present disclosure.

We claim:

1. A clinical target volume delineation method applicable in an electronic device, the method comprising:
    receiving a radiotherapy computed tomography (RTCT) image;
    obtaining a plurality of binary images by delineating a gross tumor volume (GTV), lymph nodes (LNs), and organs at risk (OARs) in the RTCT image;
    calculating a signed distance map (SDM) for each of the binary images;
    inputting the RTCT image and all the SDM into a clinical target volume (CTV) delineation model;
    delineating a CTV in the RTCT image by the CTV delineation model: and
    displaying a user interface on a display of the electronic device and displaying the delineated CTV on the user interface.

2. The clinical target volume delineation method of claim 1, wherein the method of obtaining a plurality of binary images by delineating a gross tumor volume (GTV), lymph nodes (LNs), and organs at risk (OARs) in the RTCT image comprises:
    delineating the GTV and the LNs in the RTCT image to obtain a first binary image; and
    delineating the ORAs in the RTCT image by at least one pre-trained delineation model to obtain at least one second binary image.

3. The clinical target volume delineation method of claim 2, wherein the method of delineating the GTV and the LNs in the RTCT image to obtain a first binary image comprises:
    displaying a user interface on a display of the electronic device, the RTCT image being displayed on the user interface; and
    obtaining the first binary image corresponding to the GTV and the LNs by receiving the GTV and the LNs in the RTCT image manually delineated by a user.

4. The clinical target volume delineation method of claim 2, wherein the ORAs comprises: a heart region, a lung region, and a spinal cord;
    wherein the method of delineating the ORAs in the RTCT image by at least one pre-trained delineation model to obtain at least one second binary image comprises:
    inputting the RTCT image into a pre-trained heart delineation model, and obtaining a second binary image corresponding to the heart region by delineating the heart region in the RTCT image by the pre-trained heart delineation model;
    inputting the RTCT image into a pre-trained lung delineation model, and obtaining a second binary image corresponding to the lung region by delineating the lung region in the RTCT image by the pre-trained lung delineation model; and
    inputting the RTCT image into a pre-trained spinal cord delineation model, and obtaining a second binary image corresponding to the spinal cord region by delineating the spinal cord region in the RTCT image by the pre-trained spinal cord delineation model.

5. The clinical target volume delineation method of claim 1, further comprising:
    collecting a plurality of RTCT images;
    obtaining a plurality of binary images corresponding to each of the collected RTCT images by delineating a GTV, LNs, and OARs in each of the collected RTCT images;
    calculating a SDM for each of the obtained binary images;
    enhancing each the calculated SDM; and
    inputting the RTCT images and all the enhanced SDM to a 3D progressive holistically nested network (PHNN) for training to obtain the CTV delineation model.

6. The clinical target volume delineation method of claim 5, wherein the method of enhancing each the calculated SDM comprises:
    jittering each pixel point in each the calculated SDM within a preset range, wherein the jittering comprises: spatial translations.

7. The clinical target volume delineation method of claim 6, after calculating a SDM for each of the binary images, the method further comprising:
    fixing the RTCT images and all the SDM to a preset size; and extracting a preset number of volume of interest (VOI) patches from the RTCT images and all the SDM.

8. An electronic device, comprising:
at least one processor; and
a storage device storing one or more programs which when executed by the at least one processor, causes the at least one processor to:
receive a radiotherapy computed tomography (RTCT) image;
obtain a plurality of binary images by delineating a gross tumor volume (GTV), lymph nodes (LNs), and organs at risk (OARs) in the RTCT image;
calculate a signed distance map (SDM) for each of the binary images;
input the RTCT image and all the SDM into a clinical target volume (CTV) delineation model;
delineate a CTV in the RTCT image by the CTV delineation model; and
display a user interface on a display of the electronic device and display the delineated CTV on the user interface.

9. The electronic device of claim 8, wherein the at least one processor to obtain a plurality of binary images by delineating a gross tumor volume (GTV), lymph nodes (LNs), and organs at risk (OARs) in the RTCT image comprises:
delineate the GTV and the LNs in the RTCT image to obtain a first binary image; and
delineate the ORAs in the RTCT image by at least one pre-trained delineation model to obtain at least one second binary image.

10. The electronic device of claim 9, wherein the at least one processor to delineate the GTV and the LNs in the RTCT image to obtain a first binary image comprises:
display a user interface on a display of the electronic device, the RTCT image being displayed on the user interface;
obtain the first binary image corresponding to the GTV and the LNs by receiving the GTV and the LNs in the RTCT image manually delineated by a user.

11. The electronic device of claim 9, wherein the ORAs comprises:
a heart region, a lung region, and a spinal cord;
wherein the at least one processor to delineate the ORAs in the RTCT image by at least one pre-trained delineation model to obtain at least one second binary image comprises:
input the RTCT image into a pre-trained heart delineation model, and obtain a second binary image corresponding to the heart region by delineating the heart region in the RTCT image by the pre-trained heart delineation model;
input the RTCT image into a pre-trained lung delineation model, and obtain a second binary image corresponding to the lung region by delineating the lung region in the RTCT image by the pre-trained lung delineation model; and
input the RTCT image into a pre-trained spinal cord delineation model, and obtain a second binary image corresponding to the spinal cord region by delineating the spinal cord region in the RTCT image by the pre-trained spinal cord delineation model.

12. The electronic device of claim 8, wherein the at least one processor further to:
collect a plurality of RTCT images;
obtain a plurality of binary images corresponding to each of the collected RTCT images by delineating a GTV, LNs, and OARs in each of the collected RTCT images;
calculate a SDM for each of the obtained binary images;
enhance each the calculated SDM; and
input the RTCT images and all the enhanced SDM to a 3D progressive holistically nested network (PHNN) for training to obtain the CTV delineation model.

13. The electronic device of claim 12, wherein the at least one processor to enhance each the calculated SDM comprises:
jitter each pixel point in each the calculated SDM within a preset range, wherein the jitter comprises: spatial translations.

14. The electronic device of claim 13, wherein the at least one processor further to:
fix the RTCT images and all the SDM to a preset size, after calculating the SDMs for each of the binary images;
extract a preset number of volume of interest (VOI) patches from the RTCT images and all the SDM.

15. A non-transitory storage medium having stored thereon instructions that, when executed by a processor of an electronic device, causes the electronic device to perform a clinical target volume delineation method, the method comprising:
receiving a radiotherapy computed tomography (RTCT) image;
obtaining a plurality of binary images by delineating a gross tumor volume (GTV), lymph nodes (LNs), and organs at risk (OARs) in the RTCT image;
calculating a signed distance map (SDM) for each of the binary images;
inputting the RTCT image and all the SDM into a clinical target volume (CTV) delineation model;
delineating a CTV in the RTCT image by the CTV delineation model; and
displaying a user interface on a display of the electronic device and displaying the delineated CTV on the user interface.

16. The non-transitory storage medium of claim 15, wherein the method of obtaining a plurality of binary images by delineating a gross tumor volume (GTV), lymph nodes (LNs), and organs at risk (OARs) in the RTCT image comprises:
delineating the GTV and the LNs in the RTCT image to obtain a first binary image;
delineating the ORAs in the RTCT image by at least one pre-trained delineation model to obtain at least one second binary image.

17. The non-transitory storage medium of claim 16, wherein the method of delineating the GTV and the LNs in the RTCT image to obtain a first binary image comprises:
displaying a user interface on a display of the electronic device, the RTCT image being displayed on the user interface; and
obtaining the first binary image corresponding to the GTV and the LNs by receiving the GTV and the LNs in the RTCT image manually delineated by a user.

18. The non-transitory storage medium of claim 16, wherein ORAs comprises: a heart region, a lung region, and a spinal cord;
wherein the method of delineating the ORAs in the RTCT image by at least one pre-trained delineation model to obtain at least one second binary image comprises:
inputting the RTCT image into a pre-trained heart delineation model, and obtaining a second binary image corresponding to the heart region by delineating the heart region in the RTCT image by the pre-trained heart delineation model;

inputting the RTCT image into a pre-trained lung delineation model, and obtaining a second binary image corresponding to the lung region by delineating the lung region in the RTCT image by the pre-trained lung delineation model; and inputting the RTCT image into a pre-trained spinal cord delineation model, and obtaining a second binary image corresponding to the spinal cord region by delineating the spinal cord region in the RTCT image by the pre-trained spinal cord delineation model.

19. The non-transitory storage medium of claim 15, the method further comprising:

collecting a plurality of RTCT images;

obtaining a plurality of binary images corresponding to each of the collected RTCT images by delineating a GTV, LNs, and OARs in each of the collected RTCT images;

calculating a SDM for each of the obtained binary images;

enhancing each the calculated SDM; and inputting the RTCT images and all the enhanced SDM to a 3D progressive holistically nested network (PHNN) for training to obtain the CTV delineation model.

20. The non-transitory storage medium of claim 19, wherein the method of enhancing each the calculated SDM comprises:

jittering each pixel point in each the calculated SDM within a preset range, wherein the jittering comprises: spatial translations.

* * * * *